US007786172B2

(12) United States Patent
de Lignières

(10) Patent No.: US 7,786,172 B2
(45) Date of Patent: *Aug. 31, 2010

(54) TREATMENT OF MASTALGIA WITH 4-HYDROXY TAMOXIFEN

(75) Inventor: Bruno de Lignières, Draveil (FR); Gabrielle Elisabeth Brink de Lignières, legal representative, Draveil (FR)

(73) Assignee: Laboratories Besins International, Montrouge (FR)

( * ) Notice: Subject to any disclaimer, the term of this patent is extended or adjusted under 35 U.S.C. 154(b) by 966 days.

This patent is subject to a terminal disclaimer.

(21) Appl. No.: 10/734,640

(22) Filed: Dec. 15, 2003

(65) Prior Publication Data

US 2005/0032909 A1 Feb. 10, 2005

Related U.S. Application Data

(60) Provisional application No. 60/433,959, filed on Dec. 18, 2002.

(51) Int. Cl.
| | | |
|---|---|---|
| A61K 31/135 | (2006.01) | |
| A61K 31/44 | (2006.01) | |
| A61K 9/70 | (2006.01) | |
| A01N 33/02 | (2006.01) | |
| A01N 43/40 | (2006.01) | |
| A61F 13/00 | (2006.01) | |
| A61L 15/16 | (2006.01) | |

(52) U.S. Cl. .................. 514/651; 514/344; 424/449; 424/444

(58) Field of Classification Search ................ 514/651, 514/212, 551, 344; 424/449, 444
See application file for complete search history.

(56) References Cited

U.S. PATENT DOCUMENTS

| | | | |
|---|---|---|---|
| 4,919,937 | A | 4/1990 | Mauvais-Jarvis |
| 4,973,755 | A | 11/1990 | Grafe et al. |
| 5,045,553 | A | 9/1991 | Ueda et al. |
| 5,189,212 | A | 2/1993 | Ruenitz |
| 5,613,958 | A * | 3/1997 | Kochinke et al. ........... 604/307 |
| 5,720,963 | A | 2/1998 | Smith |
| 6,013,270 | A | 8/1999 | Schmidt et al. |
| 6,503,894 | B1 | 1/2003 | Dudley et al. |
| 7,485,623 | B2 | 2/2009 | Bua |
| 7,507,769 | B2 | 3/2009 | Le Nestour |
| 2002/0115676 | A1 | 8/2002 | MacLean |
| 2003/0065017 | A1 | 4/2003 | HuaZhu et al. |
| 2003/0087885 | A1 | 5/2003 | Masini-Eteve et al. |
| 2003/0153543 | A1 | 8/2003 | Tanabe et al. |
| 2004/0138314 | A1 | 7/2004 | Bua |
| 2005/0031695 | A1 | 2/2005 | Rouanet et al. |
| 2005/0032910 | A1 | 2/2005 | Palumbo et al. |
| 2005/0158388 | A1 | 7/2005 | Le Nestour et al. |
| 2005/0208139 | A1 | 9/2005 | Hilt et al. |
| 2005/0209340 | A1 | 9/2005 | Le Nestour |
| 2006/0105041 | A1 | 5/2006 | Masini-Eteve |
| 2009/0186944 | A1 | 7/2009 | Rouanet et al. |

FOREIGN PATENT DOCUMENTS

| | | |
|---|---|---|
| DE | 38 36 862 A1 | 5/1990 |
| EP | 0 792 640 A2 | 9/1997 |
| EP | 0 513 832 | 7/2000 |
| EP | 1 106 179 A2 | 6/2001 |
| EP | 1 177 787 A2 | 2/2002 |
| EP | 1 579 856 A1 | 9/2005 |
| EP | 1 579 857 A1 | 9/2005 |
| WO | WO 02/03969 A2 | 1/2002 |
| WO | WO 02/36129 A2 | 5/2002 |
| WO | WO 2004/110420 A1 | 12/2004 |

OTHER PUBLICATIONS

Bronaugh & Maibach, "Percutaneous Absorption Drugs-Cosmetics-Mechanisms-Methodology", Marcel Dekker Inc., New York, 1999.
Philip Carthew et al., "Cumulative exposure to tamoxifen: DNA adducts and liver cancer in the rat", Arch Toxicol (2001) 75: 375-380.
Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).
Eric C. Dietze et al., "Tamoxifen but Not 4-Hydroxytamoxifen Initiates Apoptosis in p53(-) Normal Human Mammary Epithelial Cells by Inducing Mitochondrial Depolarization", The Journal of Biological Chemistry vol. 276, No. 7, Issue of Feb. 16, 2001, pp. 5384-5394.
Ian S. Fentiman, "Tamoxifen and Mastalgia an Emerging Indication", Drugs, vol. 32, No. 6, Dec. 1986, pp. 477-480.
I.S. Fentiman et al., "Dosage and duration of tamoxifen treatment for mastalgia: a controlled trial", Br. J. Surg. Sep. 1988, vol. 75, No. 9, pp. 845-846.
I.S. Fentiman et al., "Studies of tamoxifen in women with mastalgia*", The British Journal of Clinical Practice, Supplement 68, vol. 43, No. 11, Nov. 1989, pp. 34-36.
N. Giambiagi et al., "Immunological Differences Between the Estradiol-, Tamxifen- and 4-Hydroxy-Tamoxifen-Estrogen Receptor Complexes Detected by Two Monoclonal Antibodies", J. Steroid Biochem. vol. 30, No. 1-6, pp. 213-217, 1988.
IBIS investigators, "First results from the International Breast Cancer Intervention Study (IBIS-I): a randomised prevention trial", The Lancet, vol. 360, Sep. 14, 2002, pp. 817-824.
V. Craig Jordan et al., "Metabolites of tamoxifen in animals and man: identification, pharmacology, and significance", Breast Cancer Research and Treatment, 2, pp. 123-138.

(Continued)

*Primary Examiner*—Sreeni Padmanabhan
*Assistant Examiner*—Umamaheswari Ramachandran
(74) *Attorney, Agent, or Firm*—Foley & Lardner LLP

(57) ABSTRACT

A method of treatment comprises administering 4-hydroxy tamoxifen percutaneously to a patient having mastalgia. The 4-hydroxy tamoxifen may be formulated in a hydroalcoholic gel or an alcoholic solution.

13 Claims, 1 Drawing Sheet

OTHER PUBLICATIONS

George G.J.M. Kuiper et al., "Comparison of the Ligand Binding Specificity and Transcript Tissue Distribution of Estrogen Receptors α and β", Endocrinology, vol. 138, No. 3, 1997, pp. 863-870.

Catherine Malet et al., "Tamoxifen and Hydroxytamoxifen Isomers *versus* Estradiol Effects on Normal Human Breast Cells in Culture", Cancer Research, vol. 48, No. 24, Dec. 15, 1988, pp. 7193-7199.

Pierre Mauvais-Jarvis et al., "trans-4-Hydroxytamoxifen Concentration and Metabolism after Local Percutaneous Adminstration to Human Breast", Cancer Research, vol. 46, Mar. 1986, pp. 1521-1525.

Henri Pujol et al., "Phase I Study of percutaneous 4-hydroxy-tamoxifen with analyses of 4-hydroxy-tamoxifen concentrations in breast cancer and normal breast tissue", Cancer Chemother. Pharmacol., 36:493-498 (1995).

David W. Robertson et al., "Synthesis of the $E$ and $Z$ Isomers of the Antiestrogen Tamoxifen and Its Metabolite, Hydroxytamoxifen, in Tritium-Labeled Form", J. Org. Chem., 1982, vol. 47, No. 12, pp. 2387-2393.

David W. Robertson et al., "Tamoxifen Antiestrogens, a Comparison of the Activity, Pharmacokinetics, and Metabolic Activation of the *Cis* and *Trans* Isomers of Tamoxifen" Journal of Steroid Biochemistry, vol. 16, pp. 1-13, (1982).

Fabrice Sauvez et al., "Cutaneously applied 4-hydroxytamoxifen is not carcinogenic in female rats", Carcinogenesis vol. 20, No. 5, pp. 843-850 1999.

John N. Wolfe MD, "Risk for Breast Cancer Development Determined by Mammographic Parenchymal Pattern", Cancer, May 1976, vol. 37, No. 5, pp. 2486-2492.

Deborah N. Ader PhD. et al., "Prevalence and impact of cyclic mastalgia in a United States clinic-based sample", Am. J. Obstet. Gynecol., vol. 177, No. 1, pp. 126-132, Jul. 1997.

M.R. Callantine PhD. et al., "Micronized 17β-Estradiol for Oral Estrogen Therapy in Menopausal Women", Obstetrics & Gynecology vol. 46, No. 1, Jul. 1975, pp. 37-41.

A. Gorins et al., "A French Double-Blind Crossover Study (Danazol Versus Placebo) in the Treatment of Severe Fibrocystic Breast Disease", Eur. J. Gynaec. Oncol. vol. 2, 1984, pp. 85-89.

S.J. Graham PhD, "Changes in Fibroglandular Volume and Water Content of Breast Tissue During the Menstrual Cycle Observed by MR Imaging at 1.5 T", JMRI, vol. 5, No. 6, Nov./Dec. 1995, pp. 695-701.

R.E. Mansel et al., "A Double Blind Trial of the Prolactin Inhibitor Bromocriptine in Painful Benign Breast Disease", Br. J. Surg. vol. 65, (1978), pp. 724-727.

Catherine S. Murphy et al., "Structure-Function Relationships of Hydroxylated Metablolites of Tamoxifen that Control the Proliferation of Estrogen-Responsive T47D Breast Cancer Cells In Vitro", Molecular Pharmacology, 38, pp. 737-743, (1990).

Lawrence H. Block, PhD, "Epidermal and Transdermal Drug Delivery", Medicated Topicals, Chapter 44, Remington: The Science and Practice of Pharmacy, Alfonso R. Gennaro, Lippincott Williams and Wilkins, 2000, pp. 836-858.

M. Sambrook et al., "Ultrasonic Doppler Study of the Hormonal Response of Blood Flow in the Normal Human Breast", Ultrasound in Med. & Biol. vol. 13, No. 3, pp. 121-129 (1987).

International Search Report of PCT/EP03/15028.

I.S. Fentiman et al., "Dosage and duration of tamoxifen treatment for mastalgia: a controlled trial", Br. J. Surg. 1988, vol. 75, September, 845-846.

Pierre Mauvais-Jarvis et al., "trans-4-Hydroxytamoxifen concentration and Metabolism after Local percutaneous Administration to Human Breast", Cancer Research 46, 1521-1525, Mar. 1986.

Henri Pujol et al, "Phase I Study of percutaneous 4-hydroxy-tamoxifen with analyses of 4-hydroxy-tamoxifen concentrations in breast cancer and normal breast tissue", Cancer Chemother Pharmacol., 1995, 36: 493-498.

Lawrence N. Parker et al, "Treatment of Gynecomastia with Tamoxifen: A Double Blind Crossover Study", Metabolism, vol. 35, No. 8, 1986: pp. 705-708.

Brisson, J., et al., Tamoxifen and Mammographic Breast Densities, Cancer Epidemiology, Biomarkers & Prevention, vol. 9, pp. 911-915 (2000).

"High Breast Density a Risk Factor", pp. 1-4, http://www.breastcancer.org/research_genetics_091902_pf.html (Aug. 11, 2005).

Mauvais-Jarvis, "Mastodynia and Fibrocystic Disease," Current Therapy in Endocrinology and Metabolism, 3:280-284 (1988).

P. Mauvais-Jarvis, "Hormonal Therapy of Benign Breast Disease," Senologie et Pathologie Mammaire. 4ème Congrès International, Paris Sep. 1-4, 1986, pp. 128-132.

U.S. Appl. No. 10/734,638 May 5, 2006 Office Action (22 pgs.).
U.S. Appl. No. 10/734,638 Oct. 2, 2006 Final Office Action (15 pgs.).
U.S. Appl. No. 10/734,638 Jan. 16, 2007 Advisory Action (4 pgs.).
U.S. Appl. No. 10/734,638 Mar. 13, 2007 Final Office Action (21 pgs.).
U.S. Appl. No. 10/734,644 Aug. 23, 2005 Office Action (10 pgs.).
U.S. Appl. No. 10/734,644 Feb. 24, 2006 Final Office Action (10 pgs.).
U.S. Appl. No. 10/734,644 Jul. 7, 2006 Advisory Action (7 pgs.).
U.S. Appl. No. 10/734,644 Apr. 10, 2007 Final Office Action (11 pgs.).

J. Barrat et al., "Effet in vivo de l'administration locale de progestérone sur l'activité mitotique des galactophores humains", J. Gynecol. Obstet. Biol. Reprod. 19: 269-274 1990.

Frédérique Kuttenn et al., "Médecine et Thérapeutique", C.R. Acad. Sc. Paris, , Série III, No. 12, 1985, 300:457-461.

P. Mauvais-Jarvis, "Le traitement hormonal des mastopathies benignes", Bull Cancer (1991) 78, 365-371.

Wijayaratne, Ashini L, et al.; "Comparative Analyses of Mechanistic Differences Among Antiestrogens"; Endocrinology; vol. 140, No. 12; USA, 1999, pp. 5828-5840.

Malet, Catherine et al.; "Effect of 4-hydroxytamoxifen isomers on growth and ultrastructural aspects of normal human breast epithelial (HBE) cells in culture"; Journal of Steroid Biochemistry & Molecular Biology 82, 2002, pp. 289-296.

Alberti et al., "In Vivo Assessment of Enhanced Topical Delivery of Terbinafine to Human Stratum Corneum," *J. Controlled Release*, vol. 71, pp. 319-327 (2001).

Friend et al. "Simple Alkyl Esters as Skin Permeation Enhancers", *Journal of controlled Release*, vol. 9, No. 1, pp. 33-41 (Jun. 1989) Abstract.

Kutten et al., "Basis for percutaneous administration of antiestrogens in breast pathology," *Contraception Fertilite Sexualite*, vol. 19, No. 2, 1991, pp. 165-171, ABS.

Ruland et al., "Changes in Breast Density Associated with Initiation, Discontinuation and Continuing Use of Hormone Replacement Thereapy", *JAMA*, vol. 285, No. 2, Jan. 10, 2001, pp. 171-176.

Santoyo et al., "Penetration Enhancer Effects on the In Vitro Percutaneous Absorption of Piroxican Through Rat Skin", *International Journal of Pharmaceutics*, vol. 117, pp. 219-224.

Office Action dated Dec. 11, 2007 from U.S. Appl. No. 10/734,638.
Notice of Allowance dated Jun. 13, 2008 from U.S. Appl. No. 10/734,638.
Office Action dated Jan. 6, 2009 from U.S. Appl. No. 10/734,638.
Office Action dated Oct. 4, 2007 from U.S. Appl. No. 10/734,644.
Notice of Allowance dated Jun. 24, 2008 from U.S. Appl. No. 10/734,644.
Notice of Allowance dated Dec. 8, 2008 from U.S. Appl. No. 10/734,644.
Office Action dated Nov. 2, 2005 from U.S. Appl. No. 10/805,528.
Office Action dated Jul. 17, 2006 from U.S. Appl. No. 10/805,528.
Office Action dated Feb. 9, 2007 from U.S. Appl. No. 10/805,528.
Office Action dated Feb. 8, 2008 from U.S. Appl. No. 10/805,528.
Notice of Allowance dated Nov. 7, 2008 from U.S. Appl. No. 10/805,528.
Office Action dated Nov. 6, 2007 from U.S. Appl. No. 10/805,530.
Office Action dated Sep. 3, 2008 from U.S. Appl. No. 10/805,530.
Office Action dated Nov. 1, 2007 from U.S. Appl. No. 10/858,399.
Office Action dated Jun. 18, 2008 from U.S. Appl. No. 10/858,399.
Office Action dated Feb. 5, 2009 from U.S. Appl. No. 10/858,399.
Office Action dated Nov. 28, 2007 from U.S. Appl. No. 10/009,390.
Office Action dated Jul. 9, 2008 from U.S. Appl. No. 10/009,390.
Office Action dated Jan. 23, 2009 from U.S. Appl. No. 10/009,390.
Office Action issued on May 5, 2009 by the Examiner in U.S. Appl. No. 11/249,122 (US 2006/0105401).

Office Action issued on Aug. 18, 2009 by the Examiner in U.S. Appl. No. 10/858,399 (US 2005/0032910).
Office Action issued on May 19, 2009 by the Examiner in U.S. Appl. No. 10/858,399 (US 2005/0032910).
Office Action issued on Sep. 15, 2009 by the Examiner in U.S. Appl. No. 10/805,530 (US 2005/0208139).

* cited by examiner

Figure 1: Mean ± SD Plasma Concentration of 4-Hydroxy Tamoxifen in Healthy Women Following Last Cutaneous Administration (Day 25 of the Second Cycle)
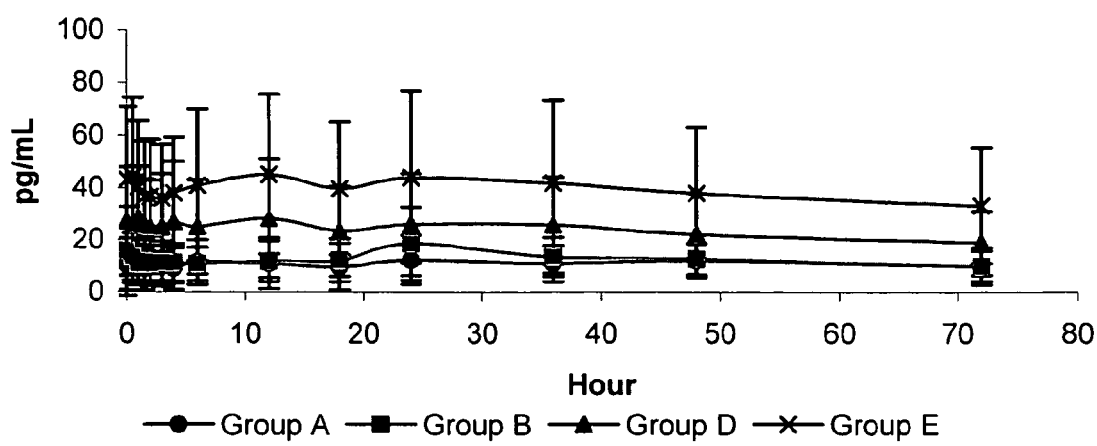

TREATMENT OF MASTALGIA WITH 4-HYDROXY TAMOXIFEN

This application claims the benefit of priority to U.S. provisional application No. 60/433,959, filed Dec. 18, 2002.

BACKGROUND OF THE INVENTION

The present invention relates to the treatment of mastalgia, or breast pain, with 4-hydroxy tamoxifen (4-OHT).

Mastalgia, also called "mastodynia," constitutes the most common breast problem for which women consult general medical practitioners. Its severity varies, but mastalgia can be so prolonged and intense as to interfere with normal daily activities, and even to disable afflicted individuals. Mastalgia can be classified according to three general sources of pain: (1) cyclical mammary pain, (2) non-cyclical mammary pain, and (3) extramammary pain. Cyclical mastalgia results from physiological breast enlargement, caused by estrogen-dependent vascular changes, during the luteal phase of the menstrual cycle (Sambrook, 1987; Graham, 1995), and affects a majority of premenopausal women. Cyclical mastalgia also can recur in postmenopausal women on estrogen replacement therapy, with a dose-dependent effect (Callantine, 1975). One recent large survey showed that 67% of women aged 18-54 experience cyclical breast discomfort during the past 6 months, with 17% of them reporting pain lasting 7 or more days monthly (Ader, 1997). "Non-cyclical mastalgia," as its name suggests, refers to pain in the breast that is not related to the menstrual cycle. A number of conditions give rise to non-cyclical mastalgia, including sclerosing adenosis, Tietz's syndrome and, rarely, breast cancer. Finally, extramammary mastalgia includes breast pain that is projected to the breast from other sources, as occurs, for example, when a patient feels pain from muscles or ribs that underlie the breasts.

Medical practitioners have experimented with many potential drug treatments for mastalgia. Non-cyclical mastalgia generally has failed to respond to drug therapy, causing some women to undergo bilateral mastectomy in extreme cases. For cyclical mastalgia, practitioners have administered diverse agents, including estrogen, androgens, pyridoxin (vitamin B6), α-tocopherol (vitamin E), bromocriptine and danazol (Fentiman, 1986). In particular, bromocriptine and danazol have shown some efficacy at relieving cyclical mastalgia, but also caused significant unwanted side effects, including nausea, vomiting, dizziness, headache, acne, sweating, amenorrhea and weight gain (Mansel et al., 1978; Gorins et al., 1984).

The cancer drug tamoxifen also has shown some promise for treating mastalgia. In several reported studies, orally administered tamoxifen reduced pain in 71-90% of patients with moderate to severe mastalgia. See Fentiman, 1986; Fentiman et al., 1988; Fentiman et al., 1989 (collectively, "Fentiman"). In subpopulations of patients with cyclical and non-cyclical mastalgia, tamoxifen reportedly was 94% and 56% effective, respectively, at reducing pain (Fentiman et al., 1988).

Tamoxifen has significant drawbacks in this context. Its action potentially impacts on every estrogen receptor in the body, and, as both an agonist and antagonist, tamoxifen provokes a wide range of systemic effects. These effects increase the risk of endometrial cancer, endometrial hyperplasia and polyps, deep vein thrombosis and pulmonary embolism, changes in liver enzyme levels, and ocular disturbances, including cataracts. Additionally, mastalgia patients treated with oral tamoxifen reported having hot flashes, vaginal discharge, depression, amenorrhea, and nausea. See Ibis, 2002; Fentiman, supra.

Thus, a treatment for mastalgia that effectively reduced pain while provoking few systemic side effects would offer significant benefit.

SUMMARY OF THE INVENTION

The present invention includes a method of treating mastalgia by administering 4-hydroxy tamoxifen. This treatment approach, preferably implemented topically, reduces pain effectively and provokes fewer systemic side effects than other treatments for mastalgia.

In performing the method of treatment, 4-hydroxy tamoxifen may be administered by any means that delivers it to estrogen receptors in vivo. As noted, it is preferable that the administration be done percutaneously (topically), to avoid the first-pass effect and related liver metabolism of the 4-hydroxy tamoxifen. For percutaneous administration, 4-hydroxy tamoxifen may be applied to any skin surface. Application to the breasts is advantageous because 4-hydroxy tamoxifen tends to concentrate in local subcutaneous tissues with estrogen receptors when administered percutaneously.

A broad range of topical formulations are suitable for performing the invention, but hydroalcoholic solutions and hydroalcoholic gels are preferred. The concentration of 4-hydroxy tamoxifen in these formulations may vary, but a dose should result in local 4-hydroxy tamoxifen concentrations that effectively oppose estrogenic driven effects.

BRIEF DESCRIPTION OF THE FIGURES

FIG. 1 illustrates the mean plasma concentration of 4-hydroxy tamoxifen in healthy women following cutaneous administration.

DETAILED DESCRIPTION OF THE PREFERRED EMBODIMENTS

As noted above, the present invention resides in the discovery that 4-hydroxy tamoxifen effectively treats mastalgia, particularly when administered percutaneously. Moreover, it has been discovered that 4-hydroxy tamoxifen provokes fewer unwanted side effects than other treatments for mastalgia.

The compound 4-hydroxy tamoxifen, or 1-[4-(2-N-dimethylaminoethoxy)phenyl]-1-(4-hydroxyphenyl)-2-phenyl-but-1-(Z)-ene, constitutes an active metabolite of the well characterized anti-estrogen compound, tamoxifen. Both cis and trans isomers exist, either of which, alone or in combination, are useful according to the present invention. The trans isomer, however, is preferred.

4-Hydroxy tamoxifen acts as a selective estrogen receptor modulator (SERM) that exhibits tissue-specificity for estrogen receptive tissues. In breast tissue, it functions as an estrogen antagonist. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Trans 4-hydroxy tamoxifen inhibits the growth in culture of normal human epithelial breast cells 100 fold more than trans-tamoxifen (Malet et al., 1988).

Although 4-hydroxy tamoxifen is a tamoxifen metabolite, its usefulness for treating mastalgia is not presaged by previous experience with tamoxifen itself. Tamoxifen is extensively metabolized by cytochrome P-450 in humans. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on estrogen receptor conformation. That is, estrogen receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chetrite et al., 1993).

Methods for preparing 4-hydroxy tamoxifen are well known. For example, U.S. Pat. No. 4,919,937 to Mauvais-Jarvis et al. describes a synthesis derived from Robertson and Katzenellenbogen, 1982. That synthesis occurs in several stages:

Stage 1—Reaction between 4-(β-dimethylaminoethoxy)-α-ethyldeoxybenzoin and p-(2-tetrahydropyranyloxy) phenylmagnesium bromide;

Stage 2—Separately from stage 1, formation of 1-(4-hydroxyphenyl)-2-phenyl-1-butanone by hydroxylation of 1,2-diphenyl-1-butanone;

Stage 3—Reaction between the products of stages 1 and 2 to form 1-(4-dimethylaminoethoxyphenyl)-1-[p-2-tetrahydropyranyloxy)phenyl]-2-phenylbutan-1-ol;

Stage 4—Dehydration with methanol/hydrochloric acid produces 1-[p-(β-dimethylaminoethoxy)phenyl]-trans-1-(p-hydroxyphenyl)-2-pheny-1-but-1-ene=4-OH-tamoxifen, a mixture of cis and trans isomers;

Stage 5—Separation of the cis and trans isomers by chromatography and crystallization to constant specific activity.

According to the present invention, 4-hydroxy tamoxifen may be administered in any dosage form and via any system that delivers the active compound to estrogen receptors in vivo, preferably to breast estrogen receptors. Preferably, the 4-hydroxy tamoxifen is delivered by "percutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration (through the hair follicles, sweat, and sebaceous glands), or any combination of these.

Percutaneous administration of 4-hydroxy tamoxifen offers several advantages. First, it avoids the hepatic metabolism that occurs subsequent to oral administration (Mauvais-Jarvis et al., 1986). Second, percutaneous administration significantly reduces systemic drug exposure, and the attendant risks from non-specifically activating estrogen receptors throughout the body; this, because topical 4-hydroxy tamoxifen is absorbed primarily into local tissues. In particular, when 4-hydroxy tamoxifen is percutaneously applied to breasts, high concentrations accumulate in the breast tissue, presumably due to many estrogen receptors therein, without creating a high plasma concentration (Mauvais-Jarvis et al., supra). Pursuant to the present invention, therefore, 4-hydroxy tamoxifen may be applied to any skin surface, but preferably to one or both breasts.

Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, the former will be bound preferentially to the estrogen receptors, and vice versa.

Accordingly, doses of 4-hydroxy tamoxifen that result in plasma concentrations less than about 80 pg/mL, or the mean estradiol concentration in normal premenopausal women, are preferred. More preferably, doses of 4-hydroxy tamoxifen will result in plasma concentrations less than about 50 pg/mL. The daily doses to be administered can initially be estimated based upon the absorption coefficients of 4-hydroxy tamoxifen, the breast tissue concentration that is desired, and the plasma concentration that should not be exceeded. Of course, the initial dose may be optimized in each patient, depending on individual responses.

As noted above, by targeting 4-hydroxy tamoxifen to breast tissue, high concentrations can be achieved in that tissue without simultaneously raising 4-hydroxy tamoxifen plasma levels to a point where significant systemic competition for estradiol receptors occurs. At a percutaneous dose of 2 mg/day (1 mg/breast/day), 4-hydroxy tamoxifen concentration in breast tissue exceeds normal estradiol concentrations in breast tissue by a factor of 4. (Barrat et al., 1990; Pujol et al., supra). Moreover, 4-hydroxy tamoxifen applied in this manner reaches concentrations in breast tissue that are an order of magnitude higher than concentrations in plasma, i.e., 10:1. By contrast, the breast tissue to plasma ratio of 4-hydroxy tamoxifen following oral administration of tamoxifen is about 5:1.

In a percutaneous formulation, doses on the order of 0.5 mg/day to 3 mg/day (0.25-1.5 mg/breast/day) should achieve the desired result, with doses of about 1.0 mg/day, 1.5 mg/day and 2.0 mg/day (0.5-1.0 mg/breast/day) being preferred.

Percutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a certain area of the skin, or (ii) by incorporating the therapeutically active substance into patches or transdermal delivery systems according to known technology.

The effectiveness of percutaneous drug administration depends on many factors, including drug concentration, surface area of application, time and duration of application, skin hydration, physicochemical properties of the drug, and partitioning of the drug between the formulation and the skin. Drug formulations intended for percutaneous use take advantage of these factors to achieve optimal delivery. Such formulations often contain penetration enhancers that improve percutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of percutaneous absorption include surfactants, DMSO, alcohol, acetone, propyleneglycol, polyethylene glycol, fatty acids, fatty alcohols and related molecules, pyrrolidones, urea, and essential oils. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to percutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious percutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably contain one or more penetration enhancers. Alcohols are preferred enhancers because 4-hydroxy tamoxifen is soluble in alcohol. Isopropyl myristate also is a preferred enhancer.

For percutaneous administration, 4-hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, glycerol, glycerol ethers, glycols, glycol ethers, polyethylene glycol, polypropylene glycol, non-volatile fatty alcohols, acids, esters, volatile alcoholic compounds, urea, talc, cellulose derivatives, and preservatives.

For practicing the present invention, preferred formulations contain 4-hydroxy tamoxifen in a hydroalcoholic gel. The amount of 4-hydroxy tamoxifen per 100 grams of gel may range from about 0.001 gram to about 1.0 gram. Preferably, it ranges from about 0.01 gram to about 0.1 gram. Table 1 describes the composition of two highly preferred 4-hydroxy tamoxifen gel formulations.

TABLE 1

Composition of 4-Hydroxy Tamoxifen Gel Formulations

| Ingredient | Quantity per 100 g of gel: 20 mg 4-OHT Gel | Quantity per 100 g of gel: 57 mg 4-OHT Gel |
|---|---|---|
| 4-Hydroxy Tamoxifen | 0.02 g | 0.057 g |
| 95% Ethyl Alcohol, EP | 72 g | 72 g |
| Isopropyl myristate, EP | 1 g | 1 g |
| Hydroxypropylcellulose, EP | 1.5 g | 1.5 g |
| Phosphate Buffer (pH 7, diluted 1:4) | q.s. 100 g | q.s. 100 g |

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

Reference to the following, illustrative examples will help to provide a more complete understanding of the invention.

EXAMPLE 1

Demonstration of Percutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received trans-[$^3$H]-4-hydroxy tamoxifen (80 μCi) in a 60% alcoholic solution, and 3 patients received trans-[$^3$H]-tamoxifen (80 μCi) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the trans to the cis form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast
Tumor Tissue Following Percutaneous Administration of Trans-
[$^3$H]-4-Hydroxy Tamoxifen to the Affected Breast

| Metabolites | % Metabolites in Breast Tissue | | | | |
|---|---|---|---|---|---|
| | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of trans-[$^3$H]-4-hydroxy tamoxifen

The percentage of radioactivity identified as [$^3$H]-4-hydroxy tamoxifen in breast tissue after percutaneous administration decreased slowly over seven days (from 97% to 65%). During this period a progressive isomerization of the trans isomer into the cis isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following percutaneous [$^3$H]-4-hydroxy tamoxifen administration, only 0.5% of the radioactivity administered showed in the blood.

In contrast to the near absence of 4-hydroxy tamoxifen metabolism in the breast tissue, marked metabolism occurred in blood. In blood, at 24 hours after administration, 68% of radioactivity represented 4-hydroxy tamoxifen, 18% represented N-desmethyl-4-hydroxy tamoxifen, and 11% represented bisphenol.

Peak urinary elimination occurred at a later time following percutaneous administration of 4-hydroxy tamoxifen compared to percutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that percutaneous application of 4-hydroxy tamoxifen to the breasts results in a substantial and lasting local tissue concentration of the drug, with minimal metabolism, stable and very low plasma concentrations, and slow elimination via the urine.

EXAMPLE 2

Demonstration of the Pharmacokinetics and Pharmacodynamics of Percutaneously Administered 4-OH-Tamoxifen Compared to 20 mg of Oral Tamoxifen This study compared the tissue and plasma concentrations of 4-hydroxy tamoxifen after percutaneous administration via a hydroalcoholic gel with tissue and plasma concentrations of 4-hydroxy tamoxifen after oral administration of tamoxifen. (Pujol et al.).

Thirty-one patients scheduled for breast cancer surgery were randomly assigned to 1 of 5 groups. They received treatment with either oral tamoxifen or percutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

| | | Treatment Groups | | Dose | |
|---|---|---|---|---|---|
| Group | N | Drug | Application Site | mg/breast/day | Total Daily Dose (mg/day) |
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |
| 5 | 6 | 4-OHT gel | arms, forearms, and shoulders | — | 2[b] |

[a]10 mg b.i.d.
[b]divided into 2 daily applications; 1 mg in the morning and 1 mg in the evening The 4-hydroxy tamoxifen gel (20 mg of 4-hydroxy tamoxifen/100 g of hydroalcholic gel; Besins-Iscovesco Laboratories) was packaged in a pressurized dose-metering pump that delivered 1.25 g of gel/metered dose (i.e., 0.25 mg of 4-hydroxy tamoxifen/dose).

During surgery, two samples (1 cm$^3$ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre- and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), luteinizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in anti-thrombin III and fibrinogen and a statistically significant increase in platelet and lymphocyte counts were observed in the oral tamoxifen group, consistent with the biologic effects of this drug observed in other studies.

TABLE 4

Concentrations of 4-hydroxy tamoxifen

Mean ± SD 4-hydroxy tamoxifen (Range)

| Group | N | Plasma Concentrations (pg/mL) | | Normal Tissue (pg/g) | Tumor (pg/g) |
|---|---|---|---|---|---|
| | | Day Pre-Surgery | Day of Surgery | | |
| 1 | 6 | 2326 ± 585 (1371-2959)[a] | 2317 ± 1098 (881-4176) | 10215 ± 2151 (5873-11511) | 12453 ± 3751 (9568-18904)[a] |
| 2 | 6 | 0 (0-0)[a] | 17 ± 27 (0[c]-61) | 353 ± 513 (0[d]-1317) | 1447 ± 2673 (0[f]-6889) |
| 3 | 5 | 164 ± 131 (29-279)[b] | 62 ± 71 (28-190) | 1112 ± 1125 (197-2979) | 1877 ± 2472 (345-6211) |
| 4 | 5 | 94 ± 76 (35-201)[b] | 13 ± 29 (0[c]-65) | 140 ± 130 (0[e]-270) | 552 ± 357 (271-1150) |
| 5 | 6 | 78 ± 138 (0[e]-284)[b] | 73 ± 114 (0[c]-244) | 992 ± 2195 (0[d]-5462) | 224 ± 312 (0[d]-799) |

[a] n = 5
[b] n = 4
[c] 4 patients had undetectable levels of 4-hydroxy tamoxifen (LOQ = 20 pg/ml)
[d] 3 patients had undetectable levels of 4-hydroxy tamoxifen
[e] 2 patients had undetectable levels of 4-hydroxy tamoxifen
[f] 1 patient had undetectable levels of 4-hydroxy tamoxifen

EXAMPLE 3

Demonstration of Tolerance and Pharmacokinetics of Percutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean±standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-hydroxy tamoxifen in
Healthy Women Following Daily Cutaneous Administration for Two
Menstrual Cycles

| | | Time after | Mean ± SD (Range is indicated in parenthesis) in pg/mL | | | |
|---|---|---|---|---|---|---|
| Cycle | Day | Application (hr) | 0.5 mg/day (n = 12)[1] | 1 mg/day (n = 8)[1] | 1 mg/day (n = 12)[2] | 2 mg/day (n = 12)[2] |
| First | 1 | 0 | (0-17.2) | (0-13.9) | (0-9.5) | (0-0) |
| | 7 | 24 | 6.4 ± 5.6 | 15.2 ± 9.7 | 14.4 ± 13.1 | 26.9 ± 18.2 |
| | | | (<LOQ-16.8) | (<LOQ-26.8) | (<LOQ-37.9) | (8.9-71.3) |
| | 20 | 24 | 13.6 ± 7.9 | 17.3 ± 9.5 | 18.1 ± 15.8 | 44.0 ± 29.2 |
| | | | (<LOQ-25.9) | (<LOQ-29.8) | (<LOQ-44.5) | (10.5-117.5) |
| | 25 | 24 | 23.9 ± 23.4 | 15.5 ± 6.6 | 19.8 ± 16.2 | 45.4 ± 31.0 |
| | | | (<LOQ-73.1) | (6.4-25.0) | (6.2-57.0) | (17.9-120.1) |
| Second | 7 | 24 | 25.2 ± 16.1 | 17.4 ± 11.2 | 22.2 ± 16.4 | 42.2 ± 24.8 |
| | | | (6.5-61.7) | (5.7-39.6) | (9.0-64.4) | (18.2-98.0) |
| | 20 | 24 | 15.7 ± 14.0 | 14.8 ± 6.5 | 24.4 ± 20.1 | 38.9 ± 27.1 |
| | | | (<LOQ-52.3) | (5.4-24.8) | (<LOQ-65.4) | (18.7-119.7) |
| | 25 | 0[3] | 10.8 ± 9.9 | 15.7 ± 17.1 | 27.2 ± 20.8 | 43.2 ± 27.7 |
| | | | (<LOQ-36.4) | (<LOQ-56.4) | (8.0-72.1) | (16.9-120.3) |
| | | 0.5 | 10.9 ± 7.4 | 13.5 ± 9.1 | 25.9 ± 18.7 | 44.5 ± 29.9 |
| | | | (<LOQ-26.0) | (<LOQ-27.7) | (8.7-69.2) | (13.6-124.5) |
| | | 1 | 10.4 ± 7.8 | 10.8 ± 6.6 | 28.7 ± 19.5 | 40.5 ± 25.1 |
| | | | (<LOQ-26.7) | (<LOQ-23.8) | (8.8-69.2) | (14.2-106.7) |
| | | 1.5 | 9.0 ± 8.2 | 11.8 ± 8.0 | 25.6 ± 17.8 | 36.8 ± 21.1 |
| | | | (<LOQ-25.1) | (<LOQ-23.6) | (7.5-67.0) | (15.9-90.0) |
| | | 2 | 11.8 ± 9.5 | 10.7 ± 6.9 | 25.1 ± 18.0 | 36.8 ± 21.6 |
| | | | (<LOQ-26.9) | (<LOQ-24.7) | (6.9-67.3) | (13.0-83.7) |
| | | 3 | 10.0 ± 7.9 | 11.4 ± 7.9 | 24.8 ± 20.5 | 36.1 ± 20.6 |
| | | | (<LOQ-23.1) | (<LOQ-28.1) | (9.0-69.9) | (11.9-89.4) |
| | | 4 | 9.2 ± 8.3 | 11.2 ± 7.3 | 26.8 ± 23.3 | 38.1 ± 21.2 |
| | | | (<LOQ-25.3) | (<LOQ-25.7) | (6.4-78.1) | (16.5-92.0) |
| | | 6 | 11.4 ± 8.5 | 10.7 ± 6.4 | 25.0 ± 18.2 | 41.0 ± 29.1 |
| | | | (<LOQ-26.6) | (<LOQ-22.8) | (9.0-65.3) | (14.0-123.8) |
| | | 12 | 11.0 ± 9.7 | 11.8 ± 7.8 | 28.3 ± 22.9 | 45.1 ± 30.6 |
| | | | (<LOQ-29.1) | (<LOQ-28.1) | (6.4-74.6) | (18.7-126.8) |
| | | 18 | 9.7 ± 8.8 | 12.2 ± 8.3 | 23.4 ± 17.4 | 39.8 ± 25.5 |
| | | | (<LOQ-24.9) | (<LOQ-29.6) | (8.1-57.9) | (16.0-107.3) |
| | 26 | 24 | 12.4 ± 9.4 | 18.6 ± 14.2 | 26.0 ± 19.6 | 44.0 ± 33.0 |
| | | | (<LOQ-34.4) | (<LOQ-40.1) | (8.9-61.9) | (15.8-132.5) |
| | | 36 | 10.9 ± 6.9 | 13.4 ± 7.5 | 25.7 ± 18.4 | 42.1 ± 31.5 |
| | | | (5.0-25.8) | (<LOQ-25.4) | (8.8-61.3) | (15.1-129.3) |
| | 27 | 48 | 12.1 ± 6.5 | 12.5 ± 6.0 | 22.0 ± 16.0 | 38.1 ± 25.3 |
| | | | (4.8-26.6) | (<LOQ-19.6) | (5.6-50.2) | (17.5-110.0) |
| | 28 | 72 | 9.9 ± 7.1 | 9.9 ± 5.8 | 18.9 ± 12.4 | 33.2 ± 22.2 |
| | | | (<LOQ-22.3) | (<LOQ-19.6) | (5.6-37.8) | (17.7-98.0) |
| | | +5 days | — | 5.8 ± 5.2 | 11.4 ± 8.2 | 20.4 ± 17.3 |
| | | | | (<LOQ-12.4) | (<LOQ-25.8) | (9.1-71.6) |
| | | +8 days | <LOQ | (<LOQ-17.4) | (0-14.8) | 10.8 ± 13.4 |
| | | | | | | (<LOQ-52.0) |
| | | +12 days | (maximum 9.09) | (<LOQ-7.0) | (0-<LOQ) | (0-30.4) |
| | | +20 days | 0 | <LOQ | (0-<LOQ) | (0-<LOQ) |

[1]Gel concentration was 20 mg of 4-hydroxy tamoxifen per 100 g of gel.
[2]Gel concentration was 57 mg of 4-hydroxy tamoxifen per 100 g of gel.
[3]Timepoint 0 is 24 hours after the application on Day 24 and prior to the final application on Day 25.
LOQ = limit of quantification (<5 pg/mL)

FIG. 1 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of 4-hydroxy tamoxifen in Healthy Women Following the Last Administration

| | Mean ± SD (Range is indicated in parenthesis) | | | |
| --- | --- | --- | --- | --- |
| Parameter | 0.5 mg/day (n = 12)[a] | 1 mg/day (n = 8)[a] | 1 mg/day (n = 12)[b] | 2 mg/day (n = 12)[b] |
| $C_{max}$ (pg/mL) | 17.0 ± 8.5 (7.6-34.4) | 21.0 ± 14.0 (<LOQ-40.1) | 35.1 ± 22.4 (9.9-78.1) | 51.6 ± 31.7 (22.1-132.5) |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T(1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.
$AUC_{0-24}$ = area under the concentration-time curve for 0-24 hours;
$C_{av}$ = Calculation of area under the curve over 24 hours ($AUC_{0-24}$) divided by 24 hours;
$C_{max}$ = maximal concentration in plasma;
$t_{1/2}$ = half-life;
T(1stC < LOQ) = first timepoint at which the plasma concentration was below the limit of quantification;
$t_{max}$ = time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne.

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects.

EXAMPLE 4

Demonstration of Efficacy for Percutaneous 4-Hydroxy Tamoxifen in Treating Mastalgia This study demonstrates that 4-hydroxy tamoxifen, when administered percutaneously, effectively treats mastalgia.

Forty-one patients, aged 18 to 45 years, with a history of ≧3 months of bilateral breast pain during the last 5 days of their menstrual cycle, regressing at the onset of menses, were enrolled in the study. All patients had normal mammograms within the previous 6 months, and utilized contraception throughout the study and 3 months preceding it.

Each patient received treatment for 6 months: 3 months with placebo gel and 3 months with active gel. The active gel (20 mg of 4-hydroxy tamoxifen/100 g of gel) was dispensed from a container with a pressurized dose-metering pump that delivered 1.25 g of gel/metered dose (i.e., 0.25 mg of 4-hydroxy tamoxifen/metered dose). The placebo gel was dispensed in the same manner, and had identical composition to the active gel, only without 4-hydroxy tamoxifen. Each patient applied one metered dose (0.25 mg of 4-hydroxy tamoxifen) of gel on each breast every day from the eighth day of her cycle until the onset of menstruation.

The primary criteria considered were the number of painful days per month and the mean pain severity during the last 10 days of the menstrual cycle. Assessments of pain were made by patient self-evaluation. Secondary criteria included clinical assessment by the physician of breast tenderness, nodularity, breast size, local warmth, and breast circumference. Any side effects were recorded.

Thirty-five of the 41 patients enrolled were evaluated for efficacy. Analysis of the primary criteria (self-report of pain) and secondary criteria (clinical examination for breast tenderness, nodularity, pain on palpation, local warmth, and breast measurement) revealed no statistically significant differences between the active drug and placebo groups. Endpoints during active treatment cycles were compared to the placebo cycles within the same patient, and also according to standard cross-over design methodology, taking into account treatment effect, patient effect, and period effect. The number of painful days (greater than 20% on the visual analog scale or VAS) during treatment with the active product did not differ significantly from placebo (8.7±8.6 versus 7.2±7.4; p>0.5; ANOVA=1.7). No significant difference was observed when the number of days with pain >40%, 60%, or 80% were examined. High inter-individual variability in response was observed, however.

Nine patients continued into a second stage of the study and, depending on their clinical response, applied increased doses of 1 mg, 1.5 mg. or 2 mg of 4-hydroxy tamoxifen daily. Daily self-evaluation of pain continued as in the earlier stage.

The higher doses of 4-hydroxy tamoxifen produced significant decreases in reported pain, as shown in Tables 8 and 9.

TABLE 8

Mean Pain Intensity During the Last 10 Days of the Menstrual Cycle

| Dose of Gel | Quantity of 4-hydroxy | Mean Pain Intensity/100 |
|---|---|---|
| Placebo | 0 | 34 +/− 25 |
| 1 dose/breast | 0.5 mg/day | 38 +/− 25 |
| 2 doses/breast | 1.0 mg/day | 29 +/− 23 |
| 3 doses/breast | 1.5 mg/day | 15 +/− 19 |
| 4 doses/breast | 2.0 mg/day | 17 +/− 19 |

Anova F = 3.69
P < 0.01

TABLE 9

Mean Number of Days of Pain Level Greater than 20

| Dose of Gel | Quantity of 4-hydroxy | Mean Days with Pain |
|---|---|---|
| Placebo | 0 | 8.1 +/− 4.2 |
| 1 dose/breast | 0.5 mg/day | 9.3 +/− 5.2 |
| 2 doses/breast | 1.0 mg/day | 8.2 +/− 5.5 |
| 3 doses/breast | 1.5 mg/day | 3.6 +/− 5.2 |
| 4 doses/breast | 2.0 mg/day | 4.7 +/− 4.4 |

Anova F = 4.5
P < 0.01

A dose of 1.5 mg/day relieved pain in the majority of patients, reducing both mean pain intensity and mean number of days with pain by more than 50%. The higher dose of 2.0 mg/day produced similar results.

Cited Publications

Each of the following cited references is incorporated herein in its entirety.

Ader, D., and M. Browne, Prevalence and impact of cyclic mastalgia in a United States clinic-based sample, Am. J. Obstet. Gynecol., 177: 126-32 (1997).

Barrat, J., B. de LigniIlres, L. Marpeau, L. Larue, S. Fournier, K. Nahoul, G. Linares, H. Giorgi, and G. Contesso, Effet in vivo de l'administration locale de progestIIrone sur l'activitII mitotique des galactophores humains, J. Gynecol. Obstet. Biol. Reprod. 19:269-274 (1990) (French).

Bronaugh and Maibach, Percutaneous Absorption: Drugs Cosmetics Mechanisms Methodology, Marcel Dekker 1999.

Callantine, M., P. Martin, O. Bolding, P. Warner, and M. Greaney, Micronized 17 beta-estradiol for oral estoren therapy in menopausal women, Obstet Gynecol, 46: 37-41 (1975).

Carthew, P., P. N. Lee, R. E Edwards, R. T. Heydon, B. M. Nolan, E. A. Martin, Cumulative exposure to tamoxifen: DNA adducts and liver cancer in the rat, Arch Toxicol, 75: 375-80 (2001).

Chetrite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res, 13(4) 931-4 (July-August 1993).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Fentiman, I. S., Tamoxifen and mastalgia. An emerging indication, Drugs 32: 477-80 (1986).

Fentiman, I. S., M. Caleffi, H. Hamed, and M. A. Chaudary, Dosage and duration of tamoxifen treatment for mastalgia: a controlled trial, British Journal of Surgery 75: 845-46 (1988).

Fentiman, I. S., M. Caleffi, H. Hamed, and M. A. Chaudary, Studies of tamoxifen in women with mastalgia, British Journal of Clinical Practice, Supplement 68, 43(11): 34-36 (1989))

Giambiagi, N. and J. R. Pasqualini, Immunological differences between the estradiol-, tamoxifen and 4-hydroxytamoxifen estrogen receptor complexes detected by two monoclonal antibodies, J. Steroid Biochem, 30(1-6): 213-7 (1988).

Gorins, A., F. Perret, B. Tournant, C. Rogier, and J. Lipszyc, A French double-blind crossover study (danazol versus placebo) in the treatment of severe fibrocystic breast disease, European Journal of Gynaecological Oncology 5(2): 85-89 (1984).

Graham, S., P. Stanchev, J. Lloyd-Smith, M. Bronskill, and D. Plewes, Changes in fibroglandular volume and water content of breast tissue during the menstrual cycle observed by MR imaging, JMRI, 5: 695-701 (1995).

IBIS Investigators, First results from the International Breast Cancer Intervention Study (IBIS-I): a randomised prevention trial, Lancet, 360(9336): 817-24 (2002).

Jordan, V. C., Metabolites of tamoxifen in animals and man: identification, pharmacology, and significance, Breast Cancer Res. Treat., 2(2) 123-38 (1982).

Kuiper, G. G. J. M., B. Carlsson, K. Grandien, E. Enmark, J. Heggblad, S. Nilsson, J. Gustafsson, Comparison of the ligand binding specificity and transcript tissue distribution of estrogen receptors $\alpha$ and $\beta$, Endocrinology, 138:863-870 (1997).

Kutternn, F. and P. Mauvais-Jarvis, Intratumoral levels and metabolism of 4-hydroxytamoxifen after percutaneous administration at the breast level, C. R. Acad. Sci. III. 300:457-462 (1985) (French).

Malet C, A. Gompel, P. Spritzer, N Bricourt, N H Yaneva, I. Mowszowicz, F. Kutten and P Mauvais Jarvis, Tamoxifen and hydroxytamoxifen isomers versus estradiol effects on normal human breast cells in culture, Cancer Research, 48: 7193-7199 (1988).

Mansel, R. E., P. E. Preece, and L. E. Hughes, A double blind trial of the prolactin inhibitor bromocriptine in painful benign breast disease, British Journal of Surgery 65(10): 724-27 (1978).

Mauvais-Jarvis, P., N. Baudot, D. Castaigne, P. Banzet, and F. Kutterm, Trans-4-hydroxytamoxifen concentration and metabolism after local percutaneous administration to human breast, Cancer Research, 46:1521-1525 (1986).

Murphy, C. S., S. M. Langan-Fahey, R. McCague, and V. C. Jordan, Structure-function relationships of hydroxylated metabolites of tamoxifen that control the proliferation of estrogen-responsive T47D breast cancer cells in vitro, Mol. Pharmac. 38:737-743 (1990).

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36:493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen antiestrogens. A comparison of the activity, pharmacokinetics, and metabolic activation of the cis and trans isomers of tamoxifen, J. Steroid Biochemistry, 16(1): 1-13 (1982).

Sambrook, M., J. Bamber, H. Minasian, C. Hill, Ultrasonic doppler study of the hormonal response of blood flow in the normal human breast, Ultrason. In Med. & Biol., 13: 121-29 (1987).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Wijayaratne, A. L., S. C. Nagel, L. A. Paige, D. J. Christensen, J. D. Norris, D. M. Fowlkes, and D. P. McDonnell, Comparative Analyses of Mechanistic Difference among Antiestrogens, Endocrinology, 140(12): 5828-5840 (1999).

What is claimed is:

1. A method of treatment for mastalgia, comprising administering percutaneously to the breasts of a patient having mastalgia a composition comprising 4-hydroxy tamoxifen as the sole therapeutically active ingredient, at a dose of at least 1.5 mg/day 4-hydroxy tamoxifen.

2. A method according to claim 1, wherein said composition comprises a penetration enhancer.

3. A method according to claim 1, wherein said 4-hydroxy tamoxifen is a blend of trans and cis isomers.

4. A method according to claim 1, wherein said 4-hydroxy tamoxifen is a trans isomer.

5. A method according to claim 1, wherein greater than about 0.75 mg/breast of said 4-hydroxy tamoxifen is administered to said patient per day.

6. A method according to claim 1, wherein greater than about 1 mg/breast of said 4-hydroxy tamoxifen is administered to said patient per day.

7. A method according to claim 1, wherein said composition is a hydroalcoholic gel.

8. A method according to claim 7, wherein said hydroalcoholic gel comprises ethyl alcohol, isopropyl myristate, and hydroxypropylcellulose.

9. A method according to claim 1, wherein said composition is an alcoholic solution.

10. A method according to claim 1, wherein said mastalgia is cyclical.

11. A method according to claim 1, wherein about 0.75 mg/breast of said 4-hydroxy tamoxifen is administered to said patient per day.

12. A method according to claim 1, wherein about 1 mg/breast of said 4-hydroxy tamoxifen is administered to said patient per day.

13. A method according to claim 1, wherein about 2 mg of said 4-hydroxy tamoxifen is administered to said patient per day.

* * * * *